US012553333B1

(12) United States Patent
Gisolf et al.

(10) Patent No.: US 12,553,333 B1
(45) Date of Patent: Feb. 17, 2026

(54) FORMATION TESTER STRESS TESTING WITH DRILL PIPE SUPPLIED ACID AND/OR PROPPANT INJECTION

(71) Applicant: Schlumberger Technology Corporation, Sugar Land, TX (US)

(72) Inventors: Adriaan Gerard Gisolf, Bucharest (RO); German David Garcia, Sugar Land, TX (US); Ashers Partouche, Sugar Land, TX (US); Mikhail Charupa, Dhahran (SA); Bei Gao, Shenzhen (CN); Francois-Xavier Dubost, Paris (FR); Ahmed Moge Ali, Dhahran (SA)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 18/954,885

(22) Filed: Nov. 21, 2024

(51) Int. Cl.

| | |
|---|---|
| ***E21B 47/007*** | (2012.01) |
| ***E21B 23/06*** | (2006.01) |
| ***E21B 33/127*** | (2006.01) |
| ***E21B 49/00*** | (2006.01) |
| ***G01N 33/28*** | (2006.01) |

(52) U.S. Cl.
CPC ............ *E21B 47/007* (2020.05); *E21B 23/06* (2013.01); *E21B 33/127* (2013.01); *E21B 49/005* (2013.01); *G01N 33/2823* (2013.01)

(58) Field of Classification Search
CPC .... E21B 47/007; E21B 49/008; E21B 49/006; E21B 49/005
See application file for complete search history.

(56) References Cited

U.S. PATENT DOCUMENTS

| | | | | |
|---|---|---|---|---|
| 5,353,637 | A * | 10/1994 | Plumb | E21B 49/008 166/308.1 |
| 9,303,508 | B2 * | 4/2016 | Ramakrishnan | E21B 49/006 |
| 9,845,673 | B2 | 12/2017 | Gisolf | |
| 11,674,372 | B2 | 6/2023 | Dumont | |
| 12,134,949 | B2 | 11/2024 | Dubost | |
| 2010/0206548 | A1 * | 8/2010 | Pisio | E21B 43/26 166/250.1 |
| 2020/0379139 | A1 * | 12/2020 | Hashem | E21B 49/0875 |
| 2024/0295153 | A1 | 9/2024 | Dumont | |

FOREIGN PATENT DOCUMENTS

WO 2025166203 A1 8/2025

OTHER PUBLICATIONS

Desroches, J. et al., "Stress measurement campaign in scientific deep boreholes: focus on tool and methods", SPWLA 62nd Annual Logging Symposium, May 17, 2021, pp. 1-21.

* cited by examiner

*Primary Examiner* — Cathleen R Hutchins
(74) *Attorney, Agent, or Firm* — Kyle R. Miiller

(57) ABSTRACT

Embodiments presented provide for formation testing in geological stratum that exhibit low permeability. In embodiments, a drill pipe supplied acid and/or proppant is injected into the low permeability stratum through action of a formation tester, thereby altering the permeability of the geological stratum.

23 Claims, 4 Drawing Sheets

FORMATION TESTER STRESS TESTING WITH DRILL PIPE SUPPLIED ACID AND/OR PROPPANT INJECTION

CROSS REFERENCE TO RELATED APPLICATIONS

None.

FIELD OF THE DISCLOSURE

Aspects of the disclosure relate to formation testing. More specifically, aspects of the disclosure relate to formation testing of geological stratum using a down-hole testing apparatus. In some embodiments, stress testing is conducted with drill pipe supplied acid or proppants.

BACKGROUND

Stress testing with wireline formation testers (FT) is routinely performed in the oil industry and for carbon capture and storage projects. As time progresses and stratum become more challenging, there is an increased need to conduct stress testing.

When the permeability of a geological stratum is low, it may be desirable to inject acid or relative permeability modifier (RPM) chemicals in the fracture to increase the matrix permeability or remove water block problems or to inject a proppant into the fracture to keep the fracture open after propagation and pressure leak off. When a fluid other than borehole fluid is to be injected during a stress test with a wireline formation tester, this fluid is normally carried in a chamber in the formation tester toolstring. Such chambers normally have a volume between 1 and 6 gallons and several chambers can be combined in a single toolstring. However, considering that multiple injection cycles are often required over multiple stations, jobs that require fluid injection from downhole chambers are limiting.

With Formation Tester Deep Injection Testing (FDIT), the formation tester is conveyed with/on drill pipe (DP), and an active circulating sub connects the drill pipe with the formation tester. With this configuration, a desired fluid can be spotted in the drill pipe while the circulating sub is open. The circulating sub's connection to the borehole is then closed and the formation tester flowline is opened to the reservoir section isolated by the dual packers. Surface pumps can now push the spotted drill pipe fluid into the reservoir, bypassing the downhole pumps.

There is a need to provide apparatus and methods that are easier to operate than conventional apparatus and methods and that will allow for testing to occur in low permeability situations and conditions.

There is a further need to provide apparatus and methods that do not have the drawbacks discussed above, namely the inability to test when permeability is low.

There is a still further need to reduce economic costs associated with operations and apparatus described above with conventional tools and methods and provide the capability of testing during all types of permeability conditions.

There is a further need to allow for large volumes of fluids to be used in stress testing rather than the limited volumes of fluids currently used when only using downhole sample chambers.

SUMMARY

So that the manner in which the above recited features of the present disclosure can be understood in detail, a more particular description of the disclosure, briefly summarized below, may be had by reference to embodiments, some of which are illustrated in the drawings. It is to be noted that the drawings illustrate only typical embodiments of this disclosure and are; therefore, not to be considered limiting of its scope, for the disclosure may admit to other equally effective embodiments without specific recitation. Accordingly, the following summary provides just a few aspects of the description and should not be used to limit the described embodiments to a single concept.

In one example embodiment, a method for stress testing of at least one geological stratum is disclosed. The method may comprise conveying a formation testing apparatus on drill pipe to a testing location within the at least one geological stratum. The method may further comprise setting at least one dual packer apparatus within a wellbore for the at least one geological stratum. The method may further comprise spotting fluid at a bottom of the drill pipe. The method may further comprise closing a circulating sub within the drill pipe. The method may further comprise performing a breakdown cycle using a drill pipe fluid and at least one downhole pump, wherein the drill pipe fluid contains at least one of an acid and/or a proppant. The method may further comprise deflating the at least one dual packer.

In another example embodiment, a method for stress testing of at least one geological stratum is disclosed. The method may comprise conveying a formation testing apparatus on drill pipe to a testing location within the at least one geological stratum. The method may further comprise setting at least one dual packer apparatus within a wellbore for the at least one geological stratum. The method may further comprise spotting fluid at a bottom of the drill pipe, wherein the fluid contains an acid and a proppant. The method may further comprise closing a circulating sub within the drill pipe. The method may further comprise performing an injection and fall off sequence with a fluid having a proppant from a volume chamber within the formation testing apparatus. The method may further comprise deflating the at least one dual packer.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the drawings. It is to be noted; however, that the appended drawings illustrate only typical embodiments of this disclosure and are; therefore, not be considered limiting of its scope, for the disclosure may admit to other equally effective embodiments.

Figure 1A:
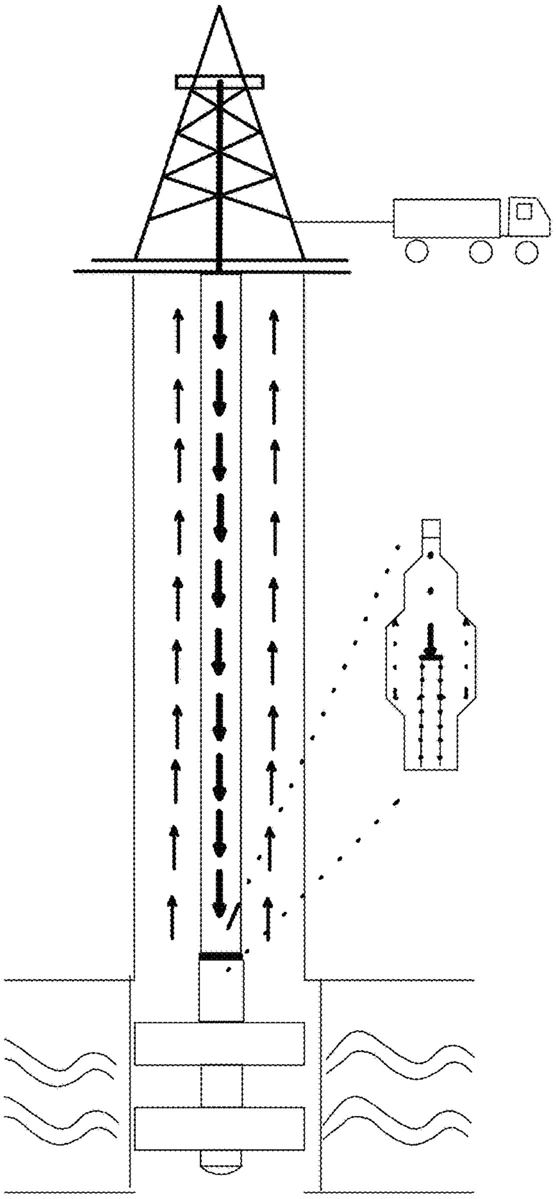
FIGS. 1A and 1B are vertical cross-sections of a deep injection tester in one example embodiment of the disclosure.

To facilitate understanding, identical reference numerals have been used, where possible, to designate identical elements that are common to the figures ("FIGS"). It is contemplated that elements disclosed in one embodiment may be beneficially utilized on other embodiments without specific recitation.

DETAILED DESCRIPTION

In the following, reference is made to embodiments of the disclosure. It should be understood; however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments, and advantages are merely illustrative and are not considered elements or limitations of the claims except where explicitly recited in a claim. Likewise, reference to "the disclosure" shall not be construed as a generalization of inventive subject matter disclosed herein and should not be considered to be an element or limitation of the claims except where explicitly recited in a claim.

Although the terms first, second, third, etc., may be used herein to describe various elements, components, regions, layers and/or sections, these elements, components, regions, layers and/or sections should not be limited by these terms. These terms may be only used to distinguish one element, components, region, layer or section from another region, layer or section. Terms such as "first", "second", and other numerical terms, when used herein, do not imply a sequence or order unless clearly indicated by the context. Thus, a first element, component, region, layer, or section discussed herein could be termed a second element, component, region, layer, or section without departing from the teachings of the example embodiments.

When an element or layer is referred to as being "on", "engaged to", "connected to", or "coupled to" another element or layer, it may be directly on, engaged, connected, coupled to the other element or layer, or interleaving elements or layers may be present. In contrast, when an element is referred to as being "directly on", "directly engaged to", "directly connected to", or "directly coupled to" another element or layer, there may be no interleaving elements or layers present. Other words used to describe the relationship between elements should be interpreted in a like fashion. As used herein, the term "and/or" includes any and all combinations of one or more of the associated listed terms.

Some embodiments will now be described with reference to the figures. Like elements in the various figures will be referenced with like numbers for consistency. In the following description, numerous details are set forth to provide an understanding of various embodiments and/or features. It will be understood; however, by those skilled in the art, that some embodiments may be practiced without many of these details, and that numerous variations or modifications from the described embodiments are possible. As used herein, the terms "above" and "below", "up" and "down", "upper" and "lower", "upwardly" and "downwardly", and other like terms indicating relative positions above or below a given point are used in this description to more clearly describe certain embodiments.

Aspects of the disclosure describe stress testing methods that utilize a large volume of spotted drill pipe fluid. These fluids are available with the FDIT hardware for wireline formation tester stress testing. The fluids may include a variety of fluids, including acids, proppants or relative permeability modifiers. In aspects of the disclosure, methods provide for injecting/propagating large volumes of acid (or other permeability enhancing fluids) or proppants into a wireline formation tester created fracture. Other method embodiments may provide for injecting/propagating volumes of acids or proppant into a fracture without flowing the injection materials through the downhole pumps. Still further method embodiments may provide for combined injection sequences utilizing both drill pipe supplied fluids and downhole volume chambers. For example, the downhole volume chamber could be used to displace the interval mud with a solids-free fluid (interval mud-solids are designed to plug the matrix pores and also mix with injected proppant, rendering these less effective).

In embodiments, for a typical hydraulic fracture in tight sand or shale formation, the size of proppant is from 40 mesh to 200 mesh (0.42 mm-0.075 mm), which is similar to solid particle size in drilling mud fluid systems. In high pressure formations, FTs can handle up to 40 percent solid content. Based on operation experience, injecting proppant from surface to downhole is a feasible concept.

Figure 1B:
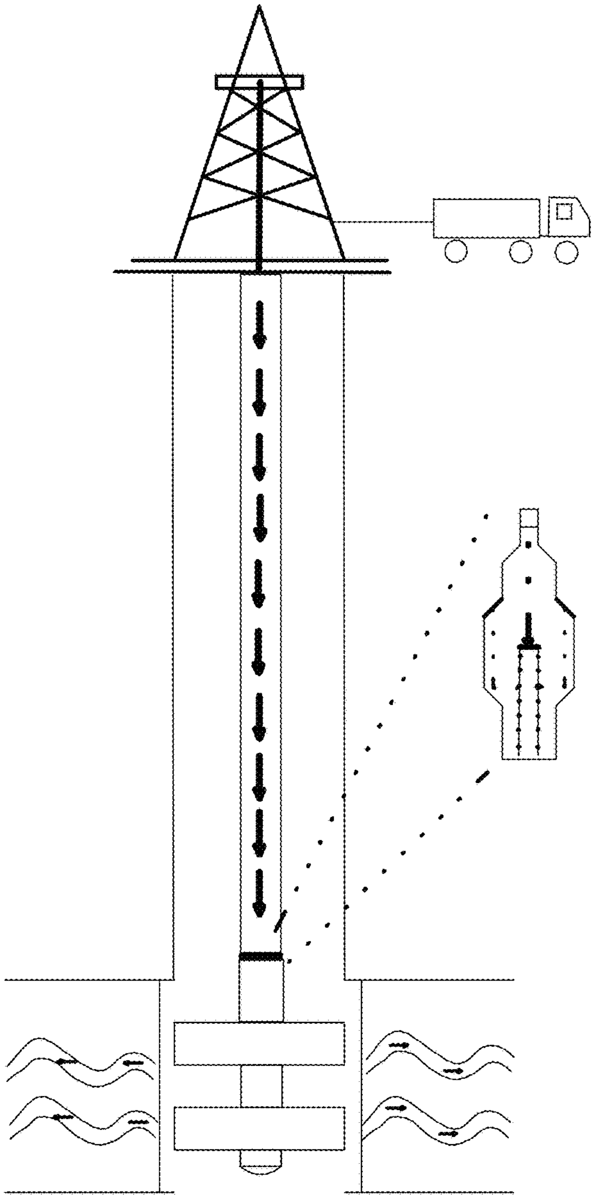

Referring to FIGS. 1A and 1B, a FDIT arrangement is illustrated. In the left part of the figure (FIG. 1A), fluid is circulated into the drill pipe and pre-existing drill pipe fluid is pushed into the annulus through the circulating sub. The annulus is open to surface, generating a return path for the borehole fluid. A predefined volume of fluid (e.g. several hundred liters) can be pumped down, followed by a spacer fluid (to separate the fluid slugs) and mud (or other injection fluid).

Once the fluid (or multiple sequences of fluids) is/are in place, which can be calculated from known drill pipe volume and measured flowrates or from formation tester fluid analyzer measurements, the circulating sub connection to the borehole is closed. FIG. 1B (right) shows the flow path when fluids in the drill pipe are forced through the formation tester flowlines and into the formation using surface pumps. An open hole scenario is depicted, but such operations can also be performed in casing, where the dual packer system straddles a perforated casing section.

In embodiments, high injection volumes and rates may be generated with FDIT, but at limited injection pressures. These limited injection pressures are present because the FDIT flowlines acts as a choke. Further complications arise as surface pressure is likely limited to 5000 psi, cable, side, entry, sub (CSES) differential rating. When the required fracture breakdown pressure is high, fracture creation (formation breakdown) can be done with the downhole pumps, optionally using borehole mud. Drill pipe supplied injection/propagation cycles may be initiated after a fracture creation cycle.

Other embodiments are possible, such as a combined technique might be used. In these embodiments, pressure may be applied simultaneously from the surface, by surface pumps into the drill pipe and additionally to downhole pumps. These pumps increase the value of absolute pressure acting on the formation surface and increase chances of fracture creation in the formation which are hard to break.

Proppant Injection

In low permeability or tight rock, it may be desirable to place acid in a fracture to increase matrix permeability or to place a proppant in the fracture so that it remains open after propagation. Testing production of a propped-open fracture is extremely challenging with formation testers because proppants are difficult to convey in sufficient quantities and because the proppant solids potentially could plug the pumps, depending on the type of proppant used. Pumping of acids could be difficult because the acid may interact with mud in the interval. Also, it might not be possible to bring a proppant mixture from the surface, downhole in the sample chamber, due to solid particles settling in the chamber. The active circulation sub will allow injection of larger volumes with different formulations and allow injection from surface bypassing the downhole pump during injection.

Figure 3:
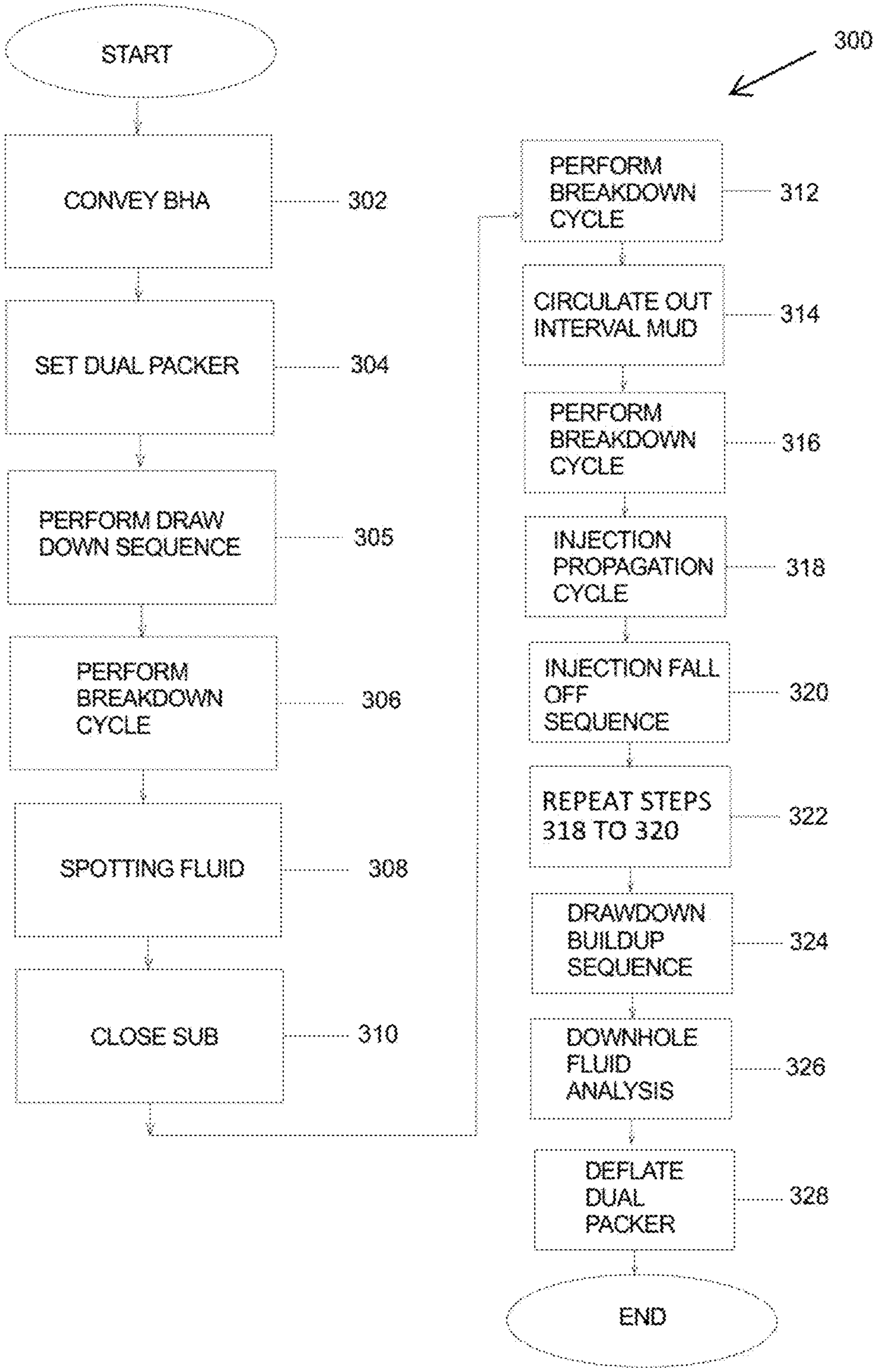
FIG. 3 is a first method of deep injection testing in one example embodiment of the disclosure.

Referring to FIG. 3, a first example method 300 of the disclosure is illustrated. The method 300 starts at 302, with conveying a BHA on drill pipe. At 304, the method 300 continues with setting a dual packer. At 305, the method 300 optionally includes performing a drawdown buildup sequence to test the matrix permeability. At 306, the method 300 optionally includes performing a breakdown cycle using the downhole pumps and mud from the borehole or DP. If the downhole pump cannot generate sufficient pressure to breakdown/fracture the formation, a surface drill pipe pressure can be applied to generate additional pressure in this breakdown cycle. At 308, the method 300 provides for spotting the fluid that is desired to be injected (e.g. proppants) at the bottom of the drill pipe with the circulating sub in open position. In embodiments, spotted fluids may be separated by a spacer fluid. In one embodiment, at least one of the spotted fluids is a proppant. At 310, the method 300 closes the FDIT circulating sub. Optionally, at 312, a breakdown cycle may be performed using the downhole pumps and either fluid from the DP or mud from the borehole. If the downhole pump cannot generate sufficient pressure to breakdown/fracture the formation, surface drill pipe pressure can be applied to generate additional pressure in this breakdown cycle.

The method 300 continues, at 314, with optionally circulating out the dual packer interval mud and circulating in the DP injection fluid—this may require a dual-inlet dual packer. The method step 314 may be repeated whenever a different DP fluid is to be injected.

The method 300 continues, wherein if step 312 was skipped, at 316, a breakdown cycle is performed using DP fluid and downhole pumps. At 318, the method 300 continues with an optional injection propagation cycle using drill pipe fluid. This is to check if sufficient propagation pressure can be generated with the downhole pumps to test propagation cycle. At 320, the method 300 continues with optionally performing an injection-fall off sequence. This may be accomplished in several different fashions, including:

- using the downhole pump to propagate the fracture using injection fluid from the DP;
- putting the flowline in bypass mode and performing injection/fall off cycles by running the surface pumps and forcing DP fluid from the drill pipe through a flowline and into the fracture;
- using the downhole pump with additional pressure generated by the surface pumps to propagate the fracture using injection fluid from the DP; and/or.
- optionally using flowback techniques to close the fracture.

The method 300 may further progress, at 322, with repeating steps 318 and 320. Repeating these steps may be accomplished continually until results converge. In embodiments, one of the three bullet points above may be accomplished with the fourth bullet point. The method 300 may then progress, at 324, with optionally performing drawdown buildup sequence to test the permeability of the open fracture. The method 300 may also progress, at 326, with optionally performing a downhole fluid analysis and acquiring downhole samples of formation fluid. The method 300 may then proceed, at 328, with deflating the dual packers and moving to the next station.

Alternatives or alterations to the method 300 described may be performed. One such alternative is that the method may be applied with two or more dual packers in the formation tester string to creating multiple fractures (clusters) in a single stop. The operational sequence will have some flexibility. For example, breakdown cycles may be performed for one dual packer at the time, but a batch of proppant can be used to fracture and "prop" multiple stations multiple times, either sequentially or at the same time.

In embodiments, method 300 can function as a step to prepare a full scale (multi-stage) hydraulic fracturing operation. Fractures created in the method 300 will become the initiation point of larger scale (conventional) hydraulic fracturing operations. Having a cluster of propped fractures, as developed in the method 300, would also act as initiation points for subsequent full scale fracturing operations.

In other embodiments, fractures created in method 300 may be sufficient without follow-up, full scale, fracturing for certain applications such as data gathering, sampling, or for open-hole or slotted liner completions.

In other embodiments, the method 300 may be used with casing, where the dual packer is used to straddle a section of perforated casing.

Figure 2A:
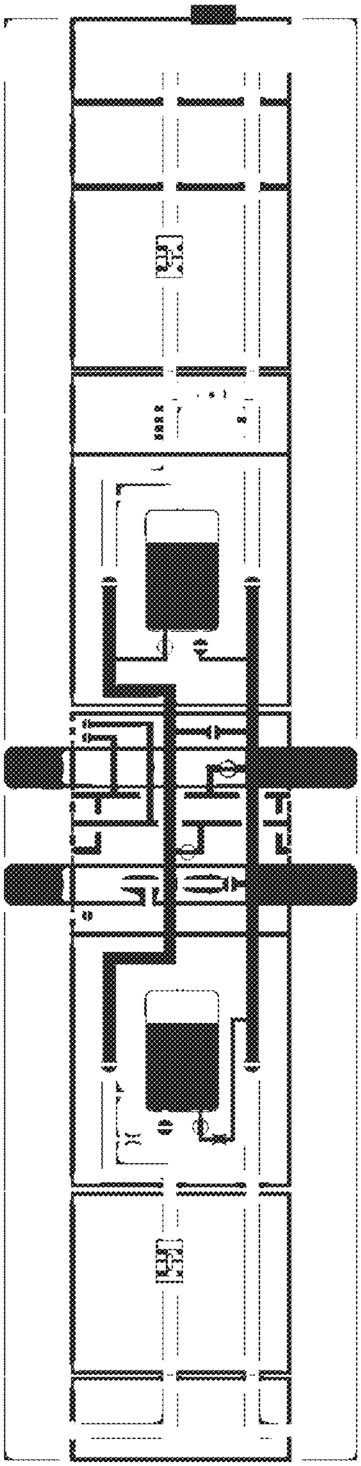
FIGS. 2A and 2B are cross-sections of formation testing strings used in one example embodiment of the disclosure.

Referring to FIG. 2A, operation downhole pumps are used to pump mud into the back of a volume chamber, with the acid or proppant on the other side of the piston being pushed into the dual packer interval. In other embodiments, it is possible to place the pump between the dual packer and volume chamber as well as pumps so that acids or proppants flow through the pump. Two chambers and pumps are shown operating at the same time. In some embodiments, the chambers and pumps may also be sequenced.

Figure 2B:
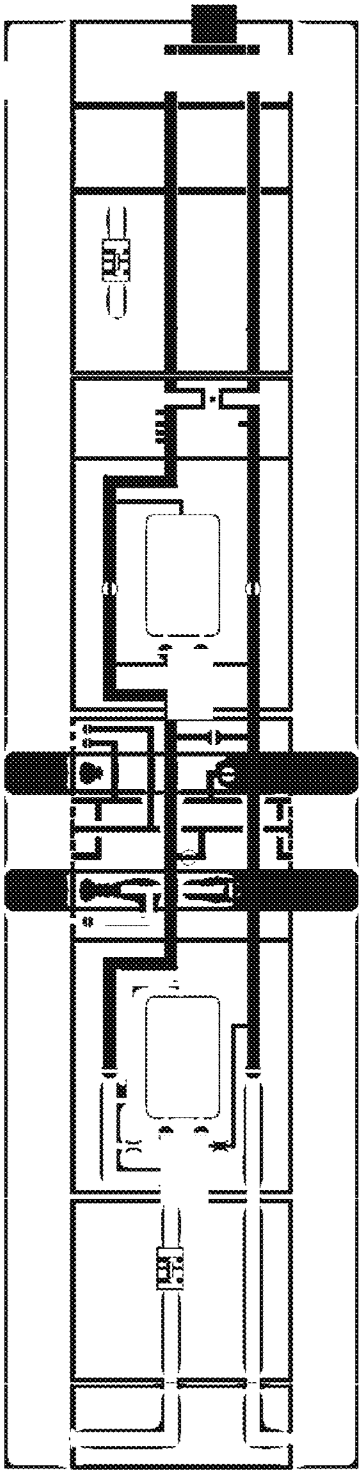

Referring to FIG. 2B, the acid or proppant has been spotted at the bottom of the drill pipe and surface pumps are used to pressure up the drill pipe and force the drill pipe fluid into the dual packer interval and into the fracture as described in the method 300 described in FIG. 3.

Figure 4:
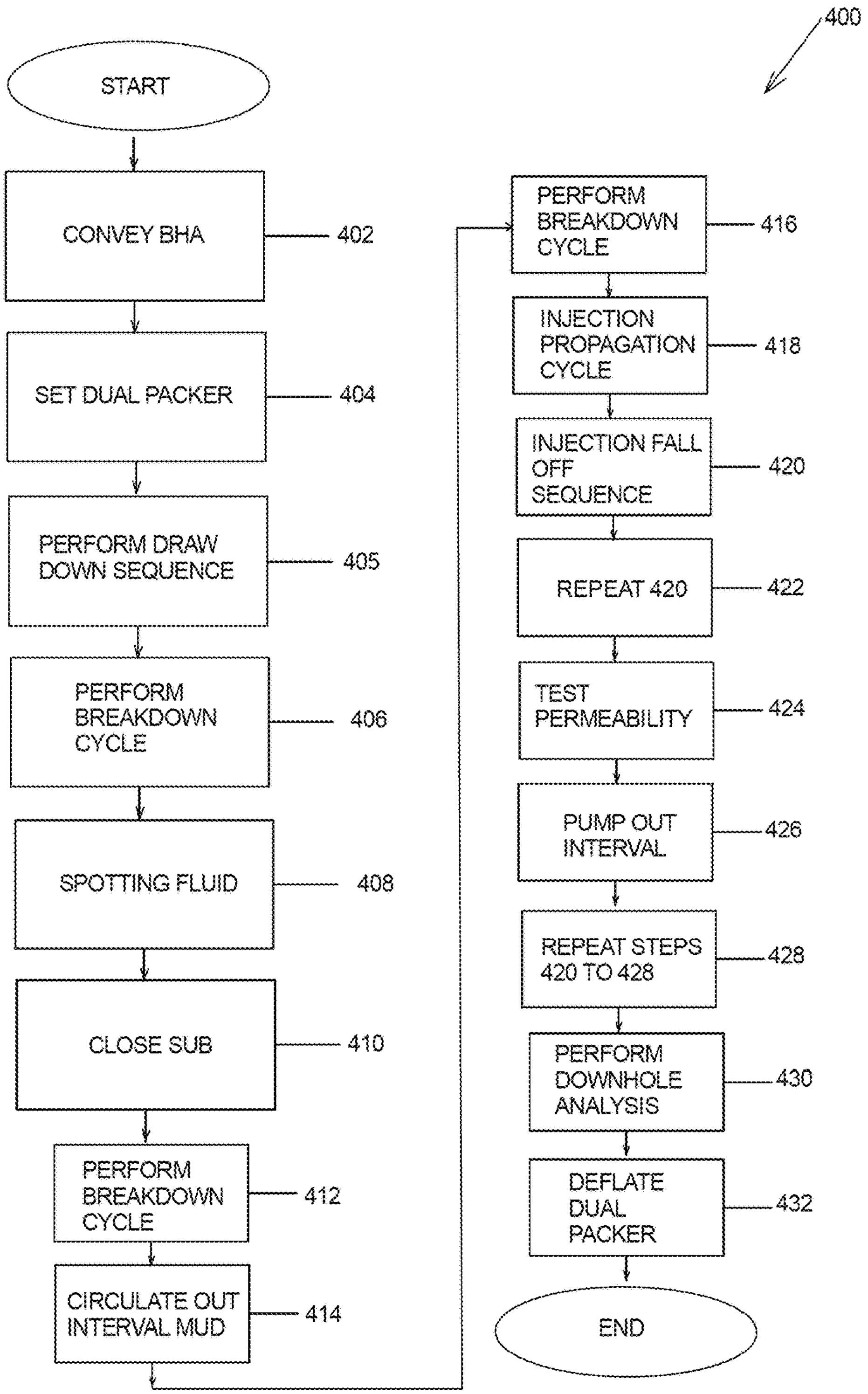
FIG. 4 is a second method of deep injection testing in one example embodiment of the disclosure.

Referring to FIG. 4, a second example method 400 of the disclosure is illustrated. The method 400 starts at 402, with conveying a BHA on drill pipe. At 404, the method 400 continues with setting a dual packer. At 405, the method 400 optionally includes performing a drawdown buildup sequence to test the matrix permeability. At 406, the method 400 optionally includes performing a breakdown cycle using the downhole pumps and mud from the borehole or DP. If the downhole pump cannot generate sufficient pressure to breakdown/fracture the formation, a surface drill pipe pressure can be applied to generate additional pressure in this breakdown cycle. At 408, the method 400 provides for spotting the fluid that is desired to be injected (e.g. proppants) at the bottom of the drill pipe with the circulating sub in open position. In embodiments, spotted fluids may be separated by a spacer fluid. In one embodiment, at least one of the spotted fluids is a proppant. At 410, the method 400 closes the FDIT circulating sub. At 412, if step 406 was skipped, the method 400 may optionally perform a breakdown cycle using the downhole pumps and either fluid from the DP or mud from the borehole. If the downhole pump cannot generate sufficient pressure to breakdown/fracture the formation, surface drill pipe pressure can be applied to generate additional pressure in this breakdown cycle.

The method 400 continues, at 414, with optionally circulating out the dual packer interval mud and circulating in the DP injection fluid—this may require a dual-inlet dual packer. The method step 414 may be repeated whenever a different DP fluid is to be injected.

The method 400 continues, wherein if steps 406 and 412 were skipped, at 416, a breakdown cycle is performed using DP fluid & downhole pumps. At 418, the method 400 continues with an optional injection propagation cycle with the downhole apparatus using drill pipe fluid or mud. This is to check if sufficient propagation pressure can be generated with the downhole pumps to test propagation cycle. At 420, the method 400 continues with optionally performing an injection-fall off sequence. In this step 420, the downhole pump may be used to propagate the fracture using injection fluid from the DP.

In another example embodiment at 420, a flowline may be put in bypass mode and injection/fall off cycles are performed by running the surface pumps and forcing DP fluid from the drill pipe through the flowline and into the fracture. In another example embodiment, the downhole pump may be used with additional pressure generated by the surface pumps to propagate the fracture using injection fluid from the DP or flowback techniques may be used to close the fracture. At 422, the method 400 continues with performing an injection-fall off sequence with proppant (or other fluids) from the volume chamber. Alternatives exist for this method step including use of the downhole pump to propagate the fracture using injection fluid from the volume chamber or use of the surface pump to drive fracture propagation using injection fluid from the volume chamber (drill pipe fluid is pumped into the side of the volume chamber which in turn drives volume chamber fluid into the fracture). In other embodiments, a downhole pump may be used with additional pressure generated by the surface pumps to propagate the fracture using injection fluid from the volume chamber. In other alternatives, flowback techniques may be used to close the fracture.

In embodiments, sequencing or alternating steps 418 and 420 allow greater flexibility in injecting different fluids sequentially into the fracture, including intermediate flows out of the interval using the downhole pump to remove residual products and precipitates created by the rock and injected fluids. In embodiments, the method 400 may optionally perform drawdown buildup sequence to test the permeability of the open fracture at 424. At 426, the method 400 may optionally pump out to flow the interval with the flow managers post-injection to remove the spent acid from a pre-flush and remove any precipitates that may form due to the presence of drilling materials at the sand face. At 428, the method 400 may optionally repeat steps 420 to 428. In further embodiments, the method 400 may, at 430, include optionally performing downhole fluid analysis and acquire downhole samples of formation fluid. The method 400 may continue, at 432, with deflating the dual packers and move to the next station.

Other alternatives to the method 400 described in relation to FIG. 4 are possible. In one such example alternative, the apparatus may have the ability to sequence fluids (using either volume chambers and/or sequenced spotted drill pipe fluids) allowing for testing of multiple formulations of treatments (pre-flush, main flush, and over-flush).

Example embodiments of FIG. 4, can also be applied with two (or more) dual packers in the formation tester string to create multiple fractures (clusters) in a single stop. The operational sequence will have some flexibility. For example, breakdown cycles would likely be performed for one dual packer at the time, but a batch of proppant can be used to fracture & "prop" multiple stations multiple times, either sequentially or at the same time.

Examples in FIG. 4, can function as a step to prepare a full scale (multi-stage) hydraulic fracturing operations. Fractures created in the method 400 will become the initiation point of larger scale (conventional) hydraulic fracturing operation. Having a cluster of propped fractures would also act as initiation points for subsequent full scale fracturing operations.

In another example embodiment, fractures created by the method 400 may be sufficient without follow-up full scale fracture for certain applications such as data gathering, sampling, or for open-hole or slotted liner completions.

Example embodiments of methods 300 and 400 may also be used in casing, where the dual packer is used to straddle a section of perforated casing.

Example embodiments of the claims are described next. These claims should not be considered limiting in the scope of the disclosure. In one example embodiment, a method for stress testing at least one geological stratum is disclosed. The method may comprise conveying a formation testing apparatus on drill pipe to a testing location within the at least one geological stratum. The method may further comprise setting at least one dual packer apparatus within a wellbore for the at least one geological stratum. The method may further comprise spotting fluid at a bottom of the drill pipe. The method may further comprise closing a circulating sub within the drill pipe. The method may further comprise performing a breakdown cycle using a drill pipe fluid and at least one downhole pump, wherein the drill pipe fluid contains at least one of an acid and a proppant. The method may further comprise deflating the at least one dual packer.

In another example embodiment, the method further comprises performing a drawdown buildup sequence to test a matrix permeability of the at least one geological stratum after the setting of the dual packer apparatus.

In another example embodiment, the method may further comprise performing a breakdown cycle using a downhole pump after the setting of the dual packer.

In another example embodiment, the method may be performed wherein the breakdown cycle is performed using mud from one of the borehole and the drill pipe.

In another example embodiment, the method may further comprise performing a breakdown cycle using a downhole pump using fluid from one of the drill pipe and mud from a borehole.

In another example embodiment, the method may further comprise performing a circulation of a mud interval defined by the dual packer.

In another example embodiment, the method may be performed wherein the spotted fluid contains a proppant.

In another example embodiment, the method may be performed wherein the spotted fluid contains at least one spacer fluid.

In another example embodiment, the method may further comprise moving to a next station for testing after the deflation of the dual packer.

In another example embodiment, the method may further comprise performing an injection propagation cycle after the performing the breakdown cycle using the drill pipe fluid and the at least one downhole pump.

In another example embodiment, the method may further comprise performing a fall-off sequence after the performing the breakdown cycle using the drill pipe fluid and the at least one downhole pump.

In another example embodiment, the method may further comprise repeating the performing of the fall-off sequence after the performing the breakdown cycle using the drill pipe fluid and the at least one downhole pump.

In another example embodiment, the method may further comprise performing a drawdown buildup sequence to test a stratum permeability.

In another example embodiment, the method may further comprise performing a downhole fluid analysis and acquiring a downhole sample of formation fluid.

In another example embodiment, the method may be performed, wherein the at least one dual packer is a dual packer.

In another example embodiment, the method may be performed, wherein the method is performed within a casing and the at least one dual packer is used to straddle a section of perforated casing.

In another example embodiment, a method for stress testing at least one geological stratum is disclosed. The method may comprise conveying a formation testing apparatus on drill pipe to a testing location within the at least one geological stratum. The method may further comprise setting at least one dual packer apparatus within a wellbore for the at least one geological stratum. The method may further comprise spotting fluid at a bottom of the drill pipe, wherein the fluid contains acid and a proppant. The method may further comprise closing a circulating sub within the drill pipe. The method may further comprise performing an injection and fall off sequence with a fluid having a proppant from a volume chamber within the formation testing apparatus. The method may further comprise deflating the at least one dual packer.

In another example embodiment, the method may further comprise performing a second injection fall off sequence.

In another example embodiment, the method may be performed wherein the injection fall off sequence includes at least one of using a downhole pump to propagate a fracture using an injection fluid from the drill pipe, placing a flowline within the testing apparatus in bypass mode and performing an injection into the stratum from surface, and afterwards using the downhole pump to propagate the fracture and using a flowback technique to close the fracture.

In another example embodiment, the method may further comprise performing a drawdown buildup sequence to test a permeability of an open fracture.

In another example embodiment, the method may further comprise performing a pump out to remove acid pumped from the injection sequence.

In another example embodiment, the method is performed within a casing and the at least one dual packer is used to straddle a section of perforated casing.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may be varied in many ways. Such variations are not to be regarded as a departure from the disclosure, and all such modifications are intended to be included within the scope of the disclosure.

While embodiments have been described herein, those skilled in the art, having benefit of this disclosure, will appreciate that other embodiments are envisioned that do not depart from the inventive scope. Accordingly, the scope of the present claims or any subsequent claims shall not be unduly limited by the description of the embodiments described herein.

What is claimed is:

1. A method for stress testing at least one geological stratum, the method comprising:

conveying a formation testing apparatus on drill pipe to a testing location within the at least one geological stratum;

setting at least one dual packer apparatus within a wellbore for the at least one geological stratum;

spotting fluid at a bottom of the drill pipe via a circulating sub of the formation testing apparatus within the drill pipe, wherein the circulating sub is in an open position for spotting the fluid;

closing the circulating sub after spotting the fluid;

performing a propagation cycle using a drill pipe fluid and at least one downhole pump, wherein the drill pipe fluid contains at least one of an acid or a proppant, and wherein the spotted fluid bypasses the at least one downhole pump via the circulating sub; and deflating the at least one dual packer apparatus.

2. The method according to claim 1, further comprising performing a drawdown buildup sequence to test a matrix permeability of the at least one geological stratum after setting the at least one dual packer apparatus.

3. The method according to claim 1, further comprising performing a breakdown cycle using the at least one downhole pump after setting the at least one dual packer apparatus.

4. The method according to claim 3, wherein the breakdown cycle is performed using mud from a borehole or fluid from the drill pipe.

5. The method according to claim 1, further comprising performing a breakdown cycle using the at least one downhole pump using fluid from one of the drill pipe or mud from a borehole.

6. The method according to claim 1, further comprising performing a circulation of a mud interval defined by the at least one dual packer apparatus.

7. The method according to claim 1, wherein the spotted fluid contains the proppant.

8. The method according to claim 1, wherein the spotted fluid contains at least one spacer fluid.

9. The method according to claim 1, further comprising moving to a next station for testing after deflating the at least one dual packer apparatus.

10. The method according to claim 1, further comprising performing the propagation cycle after performing a breakdown cycle using the drill pipe fluid and the at least one downhole pump.

11. The method according to claim 10, further comprising performing a fall-off sequence after performing the breakdown cycle using the drill pipe fluid and the at least one downhole pump.

12. The method according to claim 11, further comprising repeating the fall-off sequence after performing the breakdown cycle using the drill pipe fluid and the at least one downhole pump.

13. The method according to claim 12, further comprising performing a drawdown buildup sequence to test a stratum permeability.

14. The method according to claim 13, further comprising performing a downhole fluid analysis and acquiring a downhole sample of formation fluid.

15. The method according to claim 1, wherein the at least one dual packer apparatus comprises two dual packers.

16. The method according to claim 1, wherein the method is performed within a casing and the at least one dual packer apparatus is used to straddle a perforated section of the casing.

17. The method according to claim 1, further comprising:

performing a first drawdown buildup sequence to test a matrix permeability of the at least one geological stratum after setting the at least one dual packer apparatus;

performing a first breakdown cycle using the at least one downhole pump after performing the first drawdown buildup sequence, wherein the first breakdown cycle is performed using mud from a borehole or fluid from the drill pipe;

performing a second breakdown cycle using the at least one downhole pump after spotting the fluid and closing the circulating sub, wherein the second breakdown cycle is performed using the mud from the borehole or the fluid from the drill pipe;

performing a circulation of a mud interval defined by the at least one dual packer apparatus after performing the second breakdown cycle;

performing an injection fall off sequence after performing the circulation of the mud interval, wherein the injection fall off sequence includes using the at least one downhole pump to propagate a fracture using the drill pipe fluid, performing an injection into the at least one geological stratum with pressure generated by surface pumps to propagate the fracture, and using a flowback technique to close the fracture;

repeating the propagation cycle and the injection fall off sequence at least once;

performing a second drawdown buildup sequence after repeating the propagation cycle and the injection fall off sequence to test a permeability of an open fracture; and performing a downhole fluid analysis and acquiring a downhole sample of formation fluid after performing the second drawdown buildup sequence.

18. A method for stress testing at least one geological stratum, comprising:

conveying a formation testing apparatus on drill pipe to a testing location within the at least one geological stratum;

setting at least one dual packer apparatus within a wellbore for the at least one geological stratum;

spotting fluid at a bottom of the drill pipe via a circulating sub of the formation testing apparatus within the drill pipe, wherein the circulating sub is in an open position for spotting the fluid, wherein the spotted fluid bypasses a downhole pump via the circulating sub, wherein the fluid contains acid and a first proppant;

closing the circulating sub after spotting the fluid;

performing an injection with a fluid having a second proppant from a volume chamber within the formation testing apparatus, wherein a volume of the injection from the volume chamber is separate from any other injection; and deflating the at least one dual packer apparatus.

19. The method according to claim 18, further comprising performing an injection fall off sequence, wherein the injection fall off sequence includes using the downhole pump to propagate a fracture using a drill pipe fluid, performing an injection into the at least one geological stratum with pressure generated by surface pumps to propagate the fracture, and using a flowback technique to close the fracture.

20. The method according to claim 19, further comprising performing a drawdown buildup sequence to test a permeability of an open fracture.

21. The method according to claim 19, further comprising performing a pump out to remove acid pumped during the injection fall off sequence.

22. The method according to claim 19, wherein the method is performed within a casing and the at least one dual packer apparatus is used to straddle a perforated section of the casing.

23. The method according to claim 19, further comprising performing a first injection of fluid into the at least one geological stratum prior to the injection from the volume chamber.

* * * * *